(12) United States Patent
Fugoso et al.

(10) Patent No.: US 6,179,811 B1
(45) Date of Patent: Jan. 30, 2001

(54) IMBEDDED MARKER AND FLEXIBLE GUIDE WIRE SHAFT

(75) Inventors: Mauricio L. Fugoso, Chula Vista; Karen M. Rowean, San Diego, both of CA (US)

(73) Assignee: Medtronic, Inc., Minneapolis, MN (US)

( * ) Notice: Under 35 U.S.C. 154(b), the term of this patent shall be extended for 0 days.

(21) Appl. No.: 08/977,733

(22) Filed: Nov. 25, 1997

(51) Int. Cl.[7] .................. A61M 29/00; A61M 25/098
(52) U.S. Cl. .......................... 604/96.01; 604/529
(58) Field of Search ............................ 604/264, 200, 604/202, 96, 101

(56) References Cited

U.S. PATENT DOCUMENTS

| | | | |
|---|---|---|---|
| 4,793,359 | 12/1988 | Sharrow | 128/658 |
| 5,256,158 | 10/1993 | Tolkoff et al. | 604/280 |
| 5,300,025 | 4/1994 | Wantink | 604/96 |
| 5,458,639 | 10/1995 | Tsukashima et al. | 604/97 |
| 5,470,315 | 11/1995 | Adams | 604/96 |
| 5,480,383 | 1/1996 | Bagaoisan | 604/96 |
| 5,485,667 | 1/1996 | Kleshinski | 29/447 |
| 5,489,277 | 2/1996 | Tolkoff | 604/280 |
| 5,542,937 | * 8/1996 | Chee et al. | 604/200 |
| 5,545,138 | 8/1996 | Fugoso et al. | 604/102 |
| 5,571,089 | 11/1996 | Crocker | 604/102 |
| 5,599,326 | * 2/1997 | Carter | 604/282 |
| 5,769,819 | * 6/1998 | Schwab et al. | 604/103 |
| 5,827,225 | * 10/1998 | Ma Schwab | 604/103 |
| 5,871,468 | * 2/1999 | Kramer et al. | 604/96 |
| 5,876,376 | * 3/1999 | Schwab et al. | 604/103 |

* cited by examiner

*Primary Examiner*—Sharon Kennedy
*Assistant Examiner*—Michael J. Hayes
(74) *Attorney, Agent, or Firm*—Sterne, Kessler, Goldstein & Fox PLLC

(57) ABSTRACT

A medical catheter comprising a guide wire shaft having an inner diameter defining an inner lumen and an outer diameter, the guide wire shaft having a proximal portion and a distal portion, an inflation lumen tube defining an inflation lumen, the inflation lumen tube having a proximal end and a distal end, the guide wire shaft extending distal to the inflation lumen tube, an inflatable balloon having a proximal end and a distal end, the balloon distal end being sealingly affixed to the distal end of the inner lumen tube, the balloon proximal end being sealingly affixed to the distal end of the inflation lumen tube, the balloon being in fluid communication with the inflation lumen and at least one marker band being imbedded in the distal portion of the guide wire shaft, the marker band being positioned between the proximal end and the distal end of the inflatable balloon such that the marker band can be viewed under fluoroscopy.

11 Claims, 5 Drawing Sheets

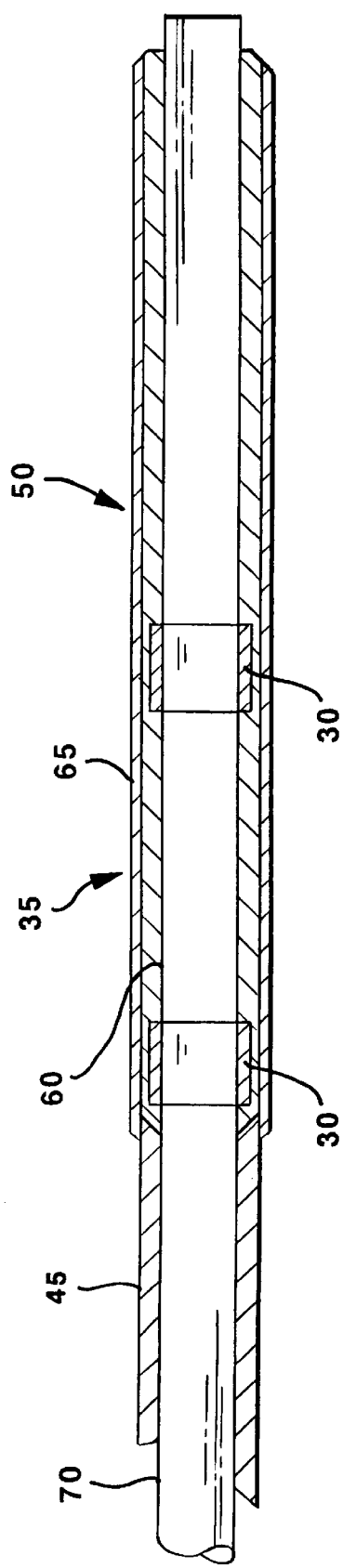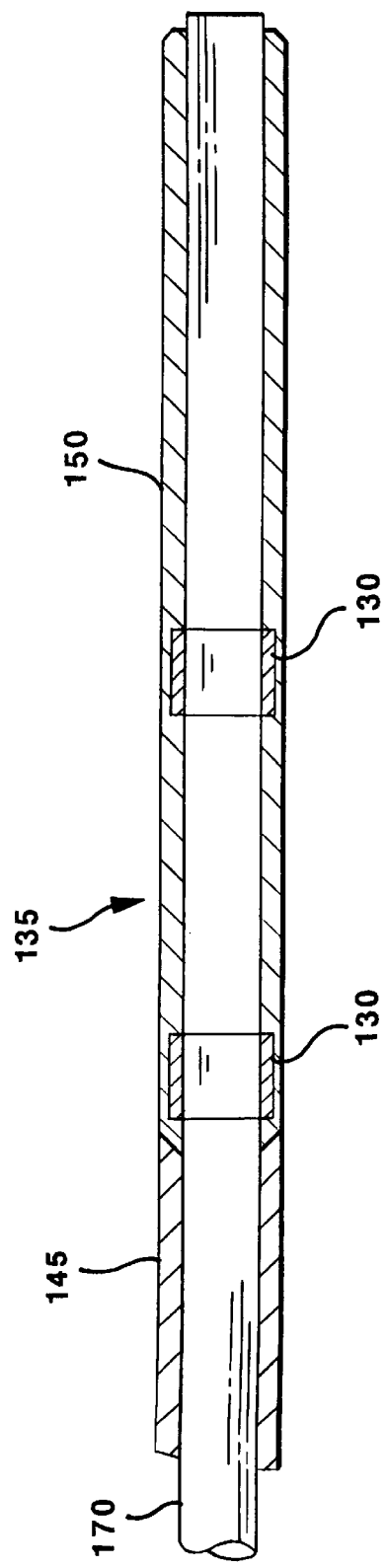
FIG.3
FIG.6

IMBEDDED MARKER AND FLEXIBLE GUIDE WIRE SHAFT

FIELD OF THE INVENTION

The present invention relates to an angioplasty catheter and more particularly to an imbedded marker band creating a flexible guide wire shaft.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guide wire of about 0.038 inches in diameter is steered through the vascular system to the site of therapy. A guiding catheter, for example, can then be advanced over the first guide wire to a point just proximal of the stenosis. The first guide wire is then removed. A balloon catheter on a smaller 0.014 inch diameter second guide wire is advanced within the guiding catheter to a point just proximal of the stenosis. The second guide wire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall.

Although the dimensions in the above example are suited to the coronary arteries, any body lumen can be treated by percutaneous transluminal angioplasty (PTA), including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

It is advantageous for a catheter to have visible marker bands on the catheter shaft that can be viewed using a fluoroscope machine to position the catheter in relation to the lesions. It is also advantageous for a catheter shaft to have a smooth outer surface with minimal bumps from the marker bands. What is needed is marker bands which can be visible using a fluoroscope and also which do not create a significant increase in diameter so that the catheter can slide easily through the lesion.

U.S. Pat. Nos. 5,489,277 and 5,256,158 to Tolkoff et al. for "Device Having a Radiopaque Marker for Endoscopic Accessories and Method of Making Same" discloses a radiopaque ring that is inserted into an expanded section of tubing, followed by the relaxation of the tube to its original dimensions. U.S. Pat. No. 5,485,667 to Kleshinski for "Method for Attaching a Marker to a Medical Instrument" discloses a marker made of tubular radiopaque shape memory material that is deformed and then slid over or into the tubing and then heated so that the shape memory material returns to its original shape and attaches to the tubing.

SUMMARY OF THE INVENTION

It is an object of the invention to provide a marker band that is imbedded into the guide wire shaft providing a smooth surface.

The present invention is accomplished by providing an apparatus and method of manufacture for a medical catheter, comprising a guide wire shaft having an inner diameter defining an inner lumen and an outer diameter, the guide wire shaft having a proximal portion and a distal portion, an inflation lumen tube defining an inflation lumen, the inflation lumen tube having a proximal end and a distal end, the guide wire shaft extending distal to the inflation lumen tube, an inflatable balloon having a proximal end and a distal end, the balloon distal end being sealingly affixed to the distal end of the inner lumen tube, the balloon proximal end being sealingly affixed to the distal end of the inflation lumen tube, the balloon being in fluid communication with the inflation lumen and at least one marker band being imbedded in the distal portion of the guide wire shaft, the marker band being positioned between the proximal end and the distal end of the inflatable balloon such that the marker band can be viewed under fluoroscopy.

BRIEF DESCRIPTION OF THE DRAWINGS

FIG. 3 is a cross-section of the distal guide wire shaft of the catheter of FIG. 2.

FIG. 6 is similar to FIG. 3

DETAILED DESCRIPTION OF THE PREFERRED EMBODIMENTS

Figure 1:
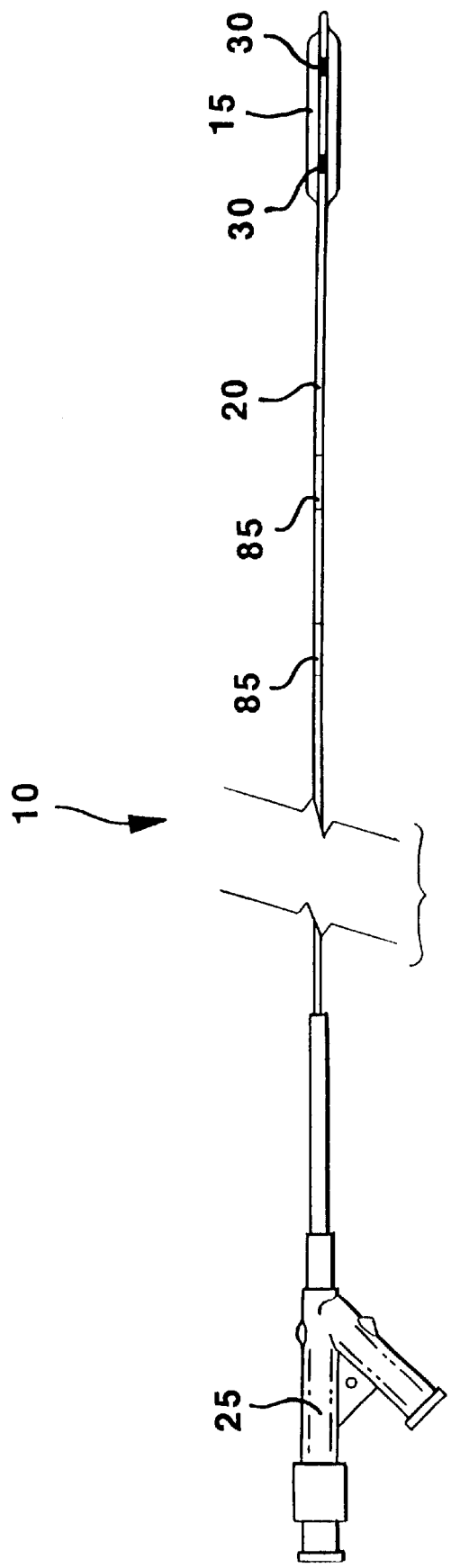
FIG. 1 is a plan view of the catheter of the invention.
Figure 2:
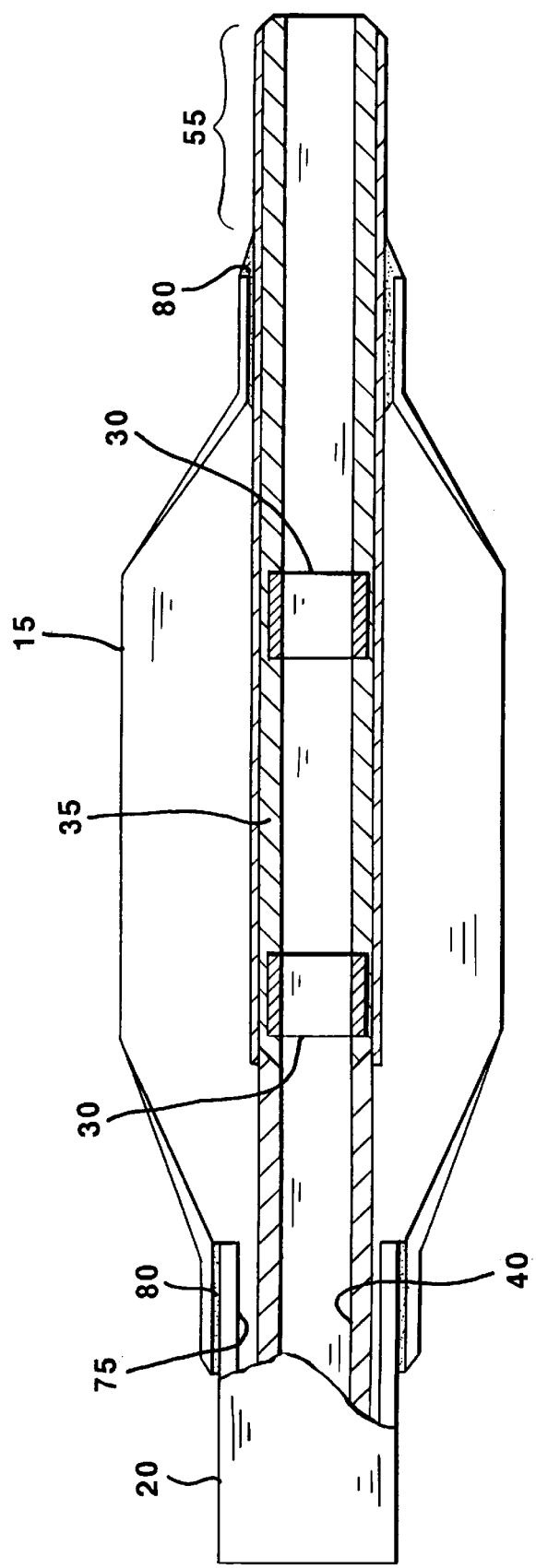
FIG. 2 is a cross-section of the distal end of the catheter of FIG. 1.

Referring to FIGS. 1 & 2, Applicant's catheter 10 is comprised of a balloon 15, shaft 20, and manifold 25. Marker bands 30 are located inside of the balloon 15. The marker bands 30 are required to position the balloon 15 using fluoroscopy during an angioplasty procedure. The intent behind the invention is to minimize the increase in diameter over the marker band 30, while enabling it to be viewed using standard fluoroscope equipment. Fluoroscope evaluations conducted using platinum/iridium marker bands 30 indicate that a wall thickness of 0.0010" is not sufficient to ensure adequate visibility, while a wall thickness of 0.0018" will enable good visibility. Traditionally, marker bands are placed on the outside of the guidewire lumen using adhesive (cyanoacrylate). This requires the inner diameter of the marker band to be large enough to enable it to be positioned onto the guide wire shaft with a sufficient gap to enable the adhesive to wick between the guide wire shaft and marker band for bonding purposes. Imbedding the marker bands 30 using the present invention creates an increase in diameter of approximately 0.005" when compared to the diameter of the guide wire shaft 35. Typical dimensions for this configuration are 0.023" over the guide wire shaft 35 and 0.028" over the marker band 30. A conventional over-the-wire design consists of a guide wire shaft 35 which defines a guide wire lumen 40 running the length of the catheter 10 inside of the shaft 20.

Imbedding the marker band 30 using the method described in this patent allows the wall thickness to be maintained to enable sufficient visibility without resulting in a significant increase in outer diameter. Samples prepared using platinum/iridium marker bands 30 with the following dimensions: 0.01675" inner diameter, 0.0018" wall, 0.051" length resulted in an increase in diameter over the marker band 30 of 0.002" when compared to the diameter of the guide wire shaft 35. Typical dimensions for this configuration were 0.0225" over the guide wire shaft 35 and 0.0245" over the marker band 30.

FIG. 2 shows the present invention. The proximal end of the balloon 15 is affixed to the distal end of the shaft 20. The guide wire shaft 35 is coaxially disposed within the shaft 20, extending through the balloon 15 with the distal end of balloon 15 being bonded to the distal end of the guide wire shaft 35. For the Balloon 15 any conventional material may be used such as Nylon, polyethylene (PE) or polyethylene terephthalate (PET). The balloon typically has one or more marker bands 30 made of a material such as platinum/iridium for visualization under fluoroscopy. Those skilled in the art would recognize that any conventional balloon design would be suitable. The balloon 15 is in fluid communication with the inflation lumen 75. The bonding of the balloon can be any conventional means such as adhesive 80, heat bonding or welding. The preferred means is to place a ring of U.V. adhesive, as for example #3311 Loctite® (manufactured by Loctite Corp. in Hartford Conn.).

The outer diameter of the shaft 20 is approximately 0.038 inches (0.96 mm) with an inner diameter of 0.0280 inches, forming an inflation lumen 75. The shaft 20 may be formed of either a stiff material for pushability (such as polyimide or poly ether ether ketone (PEEK)) or more flexible material for better tracking (such as Polyethylene (PE) or Nylon). The shaft 20 may also be made of a combination of stiff and flexible materials such that the proximal end is stiffer than the distal end. Those skilled in the art would recognize that any material which has high column strength in a thin walled configuration of the appropriate size would be suitable. The shaft 20 may have several visual marker bands 85 to indicate the various approaches, as for example, the brachial approach.

The guide wire shaft 35 is constructed from both High Density Polyethylene (HDPE) and crosslinked and expanded Low Density Polyethylene (LDPE). The guide wire shaft 35 has an inner diameter of 0.016 inches (0.41 mm) suitable for passing standard 0.014 inch (0.36 mm) guide wires. Those skilled in the art would recognize that the dimension varies depending on the application and the size of device being passed. The outer diameter of the guide wire shaft 35 is 0.023 inches. The distal end of the guide wire shaft 35 forms the catheter tip 55.

FIG. 3 shows the construction of the guide wire shaft 35. The imbedded marker bands 30 are located on a mandrel 70. The proximal portion 45 of the guide wire shaft 35 is constructed from HDPE and extends from inside of the proximal end of the balloon 15 to the manifold 25. The distal portion 50 of guide wire shaft 35 is constructed from both HDPE and LDPE and extends from the distal end of proximal portion 45 to the distal end of the catheter 10 forming the catheter tip 55. The distal portion 50 is formed with an inner layer 60 and an outer layer 65. The distal end of the proximal portion 45 is slid on the mandrel 70. The inner layer 60 is made from HDPE and is positioned over the marker bands 30 and the proximal end of the inner layer 60 overlaps the distal end of the proximal portion 45 by 0.039 inches (1.0 mm). The outer layer 65 is made from LDPE and is positioned over the inner layer 60 and the proximal end of the outer layer 65, covering the distal end of the proximal portion 45 approximately 0.197 inches (5 mm). The distal end of the proximal portion 45, the inner layer 60 and the outer layer 65 are then heated to 300–320° F., melting the inner layer 60 and the outer layer 65 onto the mandrel, covering and imbedding the marker bands 30 and bonding the inner layer 60 and the outer layer 65 to the proximal portion 45, forming the guide wire shaft 35.

Figure 4:
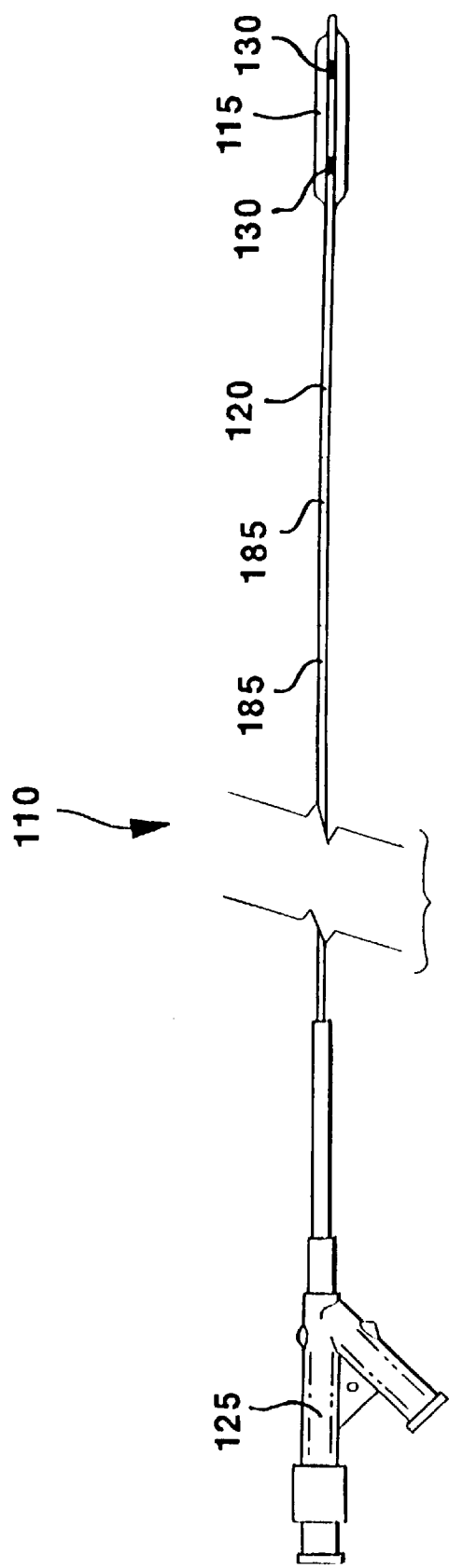
FIG. 4 is an alternate embodiment of FIG. 1
Figure 5:
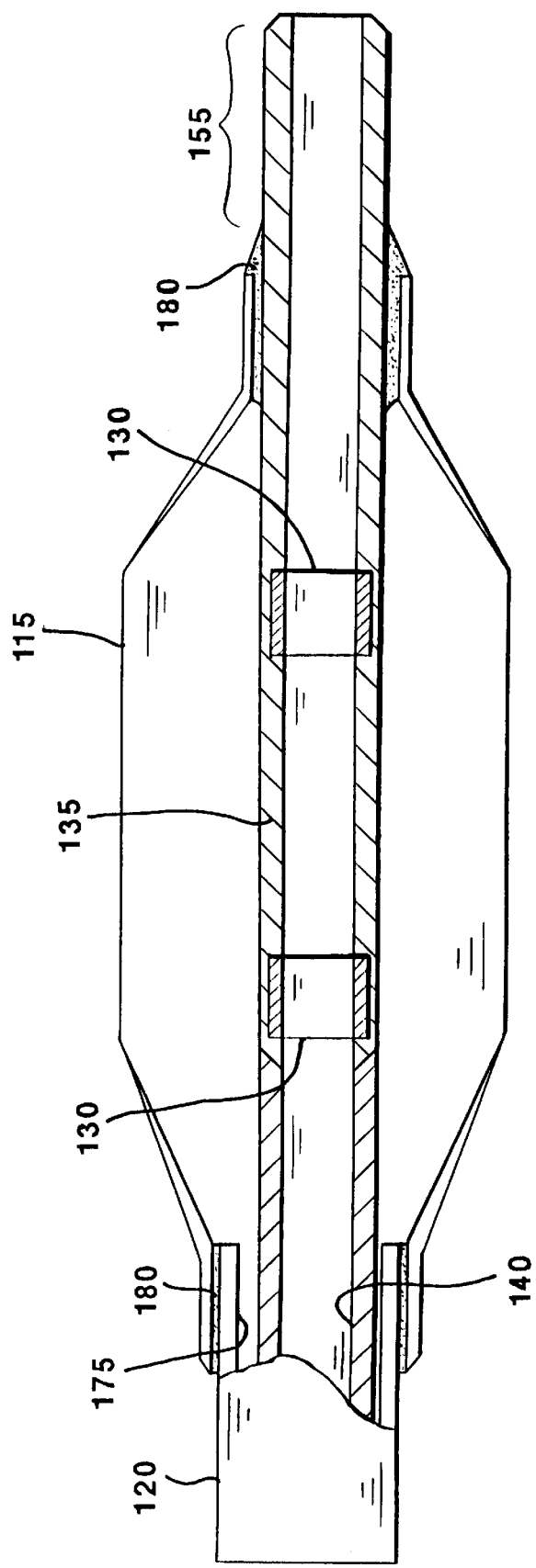
FIG. 5 is similar to FIG. 2

FIGS. 4 & 5 show catheter 110 which is comprised of a balloon 115, shaft 120, and manifold 125. Marker bands 130 are located inside of the balloon 115. The marker bands 130 are required to position the balloon 115 using fluoroscopy during an angioplasty procedure. A conventional over-the-wire design consists of a guide wire shaft 135 which defines a guide wire lumen 140 running the length of the catheter 110 inside of the shaft 120.

FIG. 5 shows the present invention. The proximal end of the balloon 115 is affixed to the distal end of the shaft 120. The guide wire shaft 135 is coaxially disposed within the shaft 120, extending through the balloon 115 with the distal end of balloon 115 being bonded to the distal end of the guide wire shaft 135. For the Balloon 115 any conventional material may be used such as nylon, polyethylene (PE) or polyethylene terephthalate (PET). The balloon typically has one or more marker bands 130 made of a material such as platinum/iridium for visualization under fluoroscopy. Those skilled in the art would recognize that any conventional balloon design would be suitable. The balloon 115 is in fluid communication with the inflation lumen 175. The bonding of the balloon can be any conventional means such as adhesive 180, heat bonding or welding. The preferred means is to place a ring of U.V. adhesive, as for example #3311 Loctite® (manufactured by Loctite Corp. in Hartford Conn.).

The outer diameter of the shaft 120 is approximately 0.038 inches (0.96 mm) with an inner diameter of 0.0280 inches, forming an inflation lumen 175. The shaft 120 may be formed of either a stiff material for pushability or more flexible material for better tracking (such as Polyethylene (PE) or Nylon). The shaft 120 may also be made of a combination of stiff and flexible materials such that the proximal end is stiffer than the distal end. Those skilled in the art would recognize that any material which has high column strength in a thin walled configuration of the appropriate size would be suitable. The shaft 120 may have several visual marker bands 185 to indicate the various approaches, as for example, the brachial approach.

The guide wire shaft 35 has an inner diameter of 0.016 inches (0.41 mm) suitable for passing standard 0.014 inch (0.36 mm) guide wires. Those skilled in the art would recognize that the dimension varies depending on the application and the size of device being passed. The outer diameter of the guide wire shaft 135 is 0.023 inches. The distal end of the guide wire shaft 135 forms the catheter tip 155.

FIG. 6 shows the construction of the guide wire shaft 135. The guide wire shaft 135 is constructed from nylon and is made in two portions, a proximal portion 145 and a distal portion 150. The imbedded marker bands 130 are located on a mandrel 170. The proximal portion 145 of the guide wire shaft 135 extends from inside of the proximal end of the balloon 115 to the manifold 125. The distal portion 150 of guide wire shaft 135 extends from the distal end of proximal portion 145 to the distal end of the catheter 110 forming the catheter tip 155. Proximal portion 145 and distal portion 150 can either be made of the same nylon or nylon having different properties, depending on what stiffness is desired The distal end of the proximal portion 145 is slid on the mandrel 170. The distal portion 150 is positioned over the marker bands 30 and butts the distal end of the proximal portion 145. The distal end of the proximal portion 45 and the distal portion 150 are then heated to 330–350° F., melting the distal portion onto the mandrel, covering and imbedding the marker bands 130 and bonding to the proximal portion 145, forming the guide wire shaft 135.

Whereas Applicant's invention depicts an imbedded marker band for an over-the-wire coronary catheter those skilled in the art would recognize that the imbedded marker bands could be used for any catheter including rapid exchange or fixed wire catheters and other applications such as peripheral etc. The preceding specific embodiments are illustrative of the practice of the invention. It is to be understood, however, that other expedients known to those skilled in the art or disclosed herein, may be employed without departing from the scope of the appended claims.

| No. | Component |
|---|---|
| 10 | Catheter |
| 15 | Balloon |
| 20 | Shaft |
| 25 | Manifold |
| 30 | Balloon Marker Bands |
| 35 | Guide Wire Shaft |
| 40 | Guide Wire Lumen |
| 45 | Proximal Portion |
| 50 | Distal Portion |
| 55 | Catheter Tip |
| 60 | Inner Layer |
| 65 | Outer Layer |
| 70 | Mandrel |
| 75 | Inflation Lumen |
| 80 | Adhesive |
| 85 | Shaft Visual Marker Bands |
| 110 | Catheter |
| 115 | Balloon |
| 120 | Shaft |
| 125 | Manifold |
| 130 | Balloon Marker Bands |
| 135 | Guide Wire Shaft |
| 140 | Guide Wire Lumen |
| 145 | Proximal Portion |
| 150 | Distal Portion |
| 155 | Catheter Tip |
| 170 | Mandrel |
| 175 | Inflation Lumen |
| 180 | Adhesive |
| 185 | Shaft Visual Marker Bands |

What is claimed is:

1. A medical catheter comprising:

a guide wire shaft having a distal end and a proximal end, an inner diameter defining an inner lumen and an outer diameter, the guide wire shaft having a proximal portion and a distal portion, the proximal portion having a proximal end and a distal end, the distal portion having a proximal end and a distal end, the distal end of the proximal portion being affixed to the proximal end of the distal portion;

an inflation lumen tube defining an inflation lumen, the inflation lumen tube having a proximal end and a distal end, the guide wire shaft distal end extending distal to the inflation lumen tube;

an inflatable balloon having a proximal end and a distal end, the balloon being in fluid communication with the inflation lumen;

at least a proximal most radiopaque marker band and a distal most radiopaque marker band each having an inner diameter and an outer diameter, the outer diameter of marker band initially being smaller than the inner diameter of each the guidewire shaft such that the guidewire shaft can be coaxially positioned over the radiopaque marker bands thereby positioning the radiopague marker band between the proximal end and the distal end of the inflatable balloon;

the radiopague marker bands being embedded into the inner diameter of the distal portion of the guidewire shaft; and the guide wire shaft distal portion having an outer layer thereon, the outer layer having a proximal end and a distal end, an inner diameter and an outer diameter, the balloon distal end being sealingly affixed to the outer layer, the outer layer proximal end extending proximal of the proximal end of the proximal most marker band, the outer layer distal end ending distally of the distal end of the distal most radiopaque marker band, the outer layer is bonded to the distal portion of the guide wire shaft, the marker band are embedded into the distal portion of the guide wire shaft such that there is no significant increase in the outer diameter of the outer layer due to the marker bands.

2. A method of making a medical catheter:

providing a guide wire shaft having an inner diameter defining an inner lumen and an outer diameter, the guide wire shaft having a proximal portion and a distal portion, the proximal portion having a proximal end and a distal end, the distal portion having a proximal end and a distal end, the distal end of the proximal portion being affixed to the proximal end of the distal portion;

providing an inflation lumen tube defining an inflation lumen, the inflation lumen tube having a proximal end and a distal end, the guide wire shaft distal end extending distal to the inflation lumen tube;

providing an inflatable balloon having a proximal end and a distal end, the balloon, being in fluid communication with the inflation lumen;

providing at least a proximal most radiopaque marker band and a distal most radiopague marker band each having an inner diameter and an outer diameter, the outer diameter of each marker band initially being smaller than the inner diameter of the guidewire shaft;

positioning the guidewire shaft coaxially over the radiopague marker bands;

positioning the radiopague marker bands between the proximal end and the distal end of the inflatable balloon;

embedding the radiopague marker bands into the inner diameter of the distal portion of the guidewire shaft;

providing a guide wire shaft distal portion having an outer layer thereon, the outer layer having a proximal end and a distal end, an inner diameter and an outer diameter, the outer layer proximal end extending proximal of the proximal end of the proximal most marker band, the outer layer distal end ending distally of the distal end of the distal most radiopaque marker band, the outer layer is bonded to the distal portion of the guide wire shaft, the distal portion of the guide wire shaft covers the marker bands, and the marker band is embedded into the distal portion of the guide wire shaft such that there are no significant increase in the outer diameter of the outer layer due to the marker bands; and sealing the balloon distal end to the outer layer.

3. A medical catheter according to claim 1 wherein the proximal portion and the distal portion of the guide wire shaft are made of the same material.

4. A medical catheter according to claim 3 wherein the proximal portion and the distal portion of the guide wire shaft are made of nylon.

5. A medical catheter according to claim 3 wherein the proximal portion and the distal portion of the guide wire shaft are made of Polyethylene (PE).

6. A medical catheter according to claim 1 wherein the distal portion of the guide wire shaft is heated and heat shrunk over the marker bands to imbed the marker bands into the guide wire shaft.

7. A medical catheter according to claim 1 wherein the proximal portion of the guide wire shaft is made of a stiffer material than the distal portion of the guide wire shaft.

8. A medical catheter according to claim 7 wherein the proximal portion of the guide wire shaft is made of High Density Polyethylene (HDPE) and the distal portion of the guide wire shaft is made of Low Density Polyethylene (LDPE).

9. A medical catheter according to claim 1 wherein the distal portion of the guide wire shaft is made of two layers of material and the proximal portion is made of one material.

10. A medical catheter according to claim 9 wherein the distal portion of the guide wire shaft is made of one inner layer of High Density Polyethylene (HDPE) and an outer layer of Low Density Polyethylene (LDPE) and the proximal portion of the guide wire shaft is made of High Density Polyethylene (HDPE).

11. A medical catheter according to claim 1 wherein the guide wire shaft is coaxial with and extends longitudinally within the inflation lumen tube.

* * * * *